USOO5792854A

United States Patent [19]
Lane et al.

[11] Patent Number: 5,792,854
[45] Date of Patent: Aug. 11, 1998

[54] DETECTION OF SALMONELLA

[75] Inventors: David J. Lane, Milford, Mass.; Ayoub Rashtchian, Gaithersburg, Md.; Kyriaki Parodos, Framingham, Mass.

[73] Assignee: Amoco Corporation, Chicago, Ill.

[21] Appl. No.: 465,987

[22] Filed: Jun. 6, 1995

Related U.S. Application Data

[63] Continuation of Ser. No. 870,804, Apr. 17, 1992, Pat. No. 5,495,008, which is a continuation of Ser. No. 127,484, Dec. 1, 1987, abandoned.

[51] Int. Cl.$^6$ .......................... C07H 21/04; C12N 15/10; C12N 15/31
[52] U.S. Cl. .................. 536/24.32; 536/24.1; 536/24.3; 436/6
[58] Field of Search .................. 435/6; 536/24.1, 536/24.3, 24.32

[56] References Cited

U.S. PATENT DOCUMENTS

| | | | |
|---|---|---|---|
| 3,755,086 | 8/1973 | Heimer | 435/6 |
| 4,139,346 | 2/1979 | Rabbani | 422/56 |
| 4,228,238 | 10/1980 | Swanson | 435/32 |
| 4,302,204 | 11/1981 | Wahl et al. | 436/501 |
| 4,358,535 | 11/1982 | Falkow et al. | 435/5 |
| 4,359,535 | 11/1982 | Pieczenik | 435/320.1 |
| 4,486,539 | 12/1984 | Ranki et al. | 436/504 |
| 4,689,295 | 8/1987 | Taber et al. | 435/6 |
| 5,519,127 | 5/1996 | Shah et al. | 536/24.32 |

FOREIGN PATENT DOCUMENTS

| | | |
|---|---|---|
| 0133671 | 3/1983 | European Pat. Off. . |
| 0146039 | 6/1985 | European Pat. Off. . |
| 2139349 | 11/1984 | United Kingdom . |
| 3402721 | 7/1984 | WIPO . |

OTHER PUBLICATIONS

Brenner et al., Journal of Bact., 98:637 (May 1969).
Kennell, Progress in Nuc. Acid Res. and Mol. Biol., 11:259 (1971).
Stoleru et al., Ann. Microbiol., 127 A:477 (1976).
Brenner et al., J. Bacteriol., 129:1435 (1977).
Cady et al., J. Clin. Microbiol., 7:265 (1978).
Nichols et al., Proc. Natl. Acad. Sci., 76:5244 (Oct. 1979).
Fox et al., "The Phylogeny of Prokaryote".
Silliker, J. of Food Protection, 43:307 (Apr., 1980).
Moseley et al., The Journal of Infectious Diseases, 142:892 (Dec., 1980).
Thomason, Journal of Food Protection, 44:381 (May 1981).
Hartman et al., Journal of Food Protection, 44: 385 (May 1981).
Woese, Scientific American, 244:98 (Jun. 1981).
Gnan et al., Journal of Food Protection, 45:4–7 (Jan. 1982).
Cleary et al., J. Bacteriol., 150:1467, (Jun 1982).
Fitts et al., Applied and Environ. Microbiol., 46:1146 (Nov. 1982).
Langer et al., Proc. Natl. Acad. Sci., 78:6633 (Nov. 1981).
Fitts, Cloning and Characterization of Salmonella–specific Sequences from *Salmonella typhimurium*, submitted to J. Bact. May, 1983.
Goor et al., Antonie van Leeuwenhock 50 (1984), pp. 302–303.
"DNA probes, monoclonals offer food industry faster Salmonella screening tests", Newswatch, vol. 4, No. 13, Jul. 2, 1984, pp. 9–10. Riggs, D&B Reports, Jul./Aug. 1984.
Fitts, "Development of a DNA–DNA Hybridization Test for the Presence of *Salmonella* in Foods", Food Technology, Mar. 1985, pp. 95–108.
Root, "Second salmonella outbreak seen", The Star, vol. 35, Apr. 11, 1985.
Reardon, "Salmonella: An epidemic unfolds", Chicago Tribune, Apr. 14, 1985.
Ritter, "IIT tests speedier salmonella detector", Sun–times, Apr. 22, 1985.
Berry, "Salmonella mystery unsolved", USA Today, May 2, 1985.
GENE–TRAK DNA Hybridization Test for Salmonella, Integrated Genetics.
Integrated Genetics, DNA Hybridization Test for Salmonella, Data Summary, Jun. 1, 1985.
"Integrated Genetics Introduces First Product: A Rapid Test For The Detection Of Salmonella In Food", Integrated Genetics for release Aug. 8, 1985.

*Primary Examiner*—David T. Fox
*Assistant Examiner*—Thanda Wai
*Attorney, Agent, or Firm*—Norval B. Galloway

[57] ABSTRACT

Nucleic acid fragments capable of hybridizing to rRNA of a Salmonella species and not capable of hybridizing to rRNA of *Escherichia coli*.

11 Claims, 16 Drawing Sheets

FIG. 3-2

```
                        1474                                                                              1527
                         |                                                                                 |
        E. coli       UGUAGCCUGCGUUUCCAGCCAAAUCCG..AAAAUCAAGGCUGAGGCGUGAUGACG
        Styphimu     -----UGU--G-------U----------U---UUCACU-U--CA----------C---
Pattern 2  Sarizona  ------------------------------------------------------------
        Eaggl PB     -----UGU--G-------U----------U---UUCACU-U--CU---------------

Styphimu     UGUAGGUGUGUUCCAGGUAAAUCCGGUUCACUUAACACUGAGGCGUCACCACG
        probe414                                   TcCACACACAAGGTCCATTTAGGCCAAGTGAAATTGTGc-5'
        probe720                                     TCCATTTAGGCCAAGTGAAATTGTGACTCCCGACT-5'
        probe846                                     TCCATTTAGGCCAAGTGAAATTGTGACTC-5'
        probe823

```
                       1707
                       |
E. coli     CGCUGAUAUGUAGCUGACGCUCCCUCCCCCAUGGAGCUGAAAUCAGUCCAAGAUA
Styphimu    ----------C-C--------A--GAU-UA-UC----------G------------
Sarizona    ----------C----------A--CGGU-UA-CCG--------G------------
Sdaress     ----------C-C--------A--GGU-UA-CC----------G------------

1755
                                                             |
Pattern 1  Styphimu    CGCUGACACGUAGGUGAAGUGAUUACUCAUGCAGCUGAAGUCAGUCCAAGAUA
           probe411               tCTCTGCATCCACTTCACTTCACTAAATGAGTAC

FIG. 5-2

```
                                          403                                                    442
                                          |                                                       |
Ecoli          5'-CGUGUAUGAAGAAGGCCUUCGGGUUGUAAGUACUUCAG
E. coli        ----------------------------------------
Salmonella     ----------------------------------------N
consensus      
Probe 683                                  cCATACTCTTCCGGAAGCCCAACATTCATGAAAGTCc-5'

443                                                                              491
                |                                                                                 |
Ecoli           UUUCAGCGGGGAGGAAGGAGUAAAGUUAAUACCUUUGCUCUCAUUGACGUUACCCGCAGAA
pattern 1       -----------------------------UGU-GUG------A-CGCAGCA---------
pattern 2       -----------------------------GA---G-C-----A-C---U----------
pattern 3       -----------------------------UGU-GUG------A-CACAGCA---------
CDCstkN55       -----------------------------CGAC--G------A-C---U-G--------- pattern 1       UUUCAGCGGGGAGGUGUUGCGUAAUACCGCAGCAAUGACGUUACCCGCAGAA
probe669        TATATCCTTCCACAACACCAACCAATTATTGCGCTCGTTAACTGCAAT-5'
probe643        cCCCCTCCTTCCACAACACCAACCAATTATTGCGCTCGTTAACTGCAAT-5'
probe676                TCCTTCCACAACACCAACCAATTATTGCGCTCGTTAACT-5'
probe778                TCCTTCCACAACACCAACCAATTATTGGCGTCGTTAACT-5'
probe776                  CCTTCCACAACACCAACCAATTATTGGCGTCGTTAAC-5'
probe806                    CACAACACCAACCAATTATTGGCGTCGTT-5'
probe807                AAAGTCGCCCCTCCTTCCACAACACCAACCAATT-5'
                                          ATTGGCGTCGTTAACTCCAATGGGTCTT-5' pattern 2       UUUCAGCGGGGAGGAAGGGGAUAAGCCUAAAUAACCUGUUGCAUUGACGUUACCCGCAGAA
probe678        TCCTTCCCCTATTCCGATTATTGGAACAAGTAACT-5' pattern 3       UUUCAGCGGGGAGGAAGGUGUUGGGUUAAUAACCAGCAAUGACGUUACCCGCAGAA
Probe786        TCCTTCCACACCAACCAATTATTGGTGTCGTTACT-5'

Pattern 4 CDCstkN55 UUUCAGCGGGGAGGAAGGCGACAAGCUUAAAUAACCUUGUUGAUGACGUUACCCGCAGAA
probe784        CTCTTCCCGTCTTCCAATTATTGGAACAACTACT-5'
```

```
                   991                                                            1045
                    |                                                               |
E. coli            5'-UUGACAUCCACGGAAGUUUCAGAGAGAAUGUGCCUUCGGGAACCGUGAGAC
S. typhimurium     ----------A----C--------GAUUG--------------U---------
S. arizona RF908   ----------A----G--------C------------------U---------
P. vulgaris       ----------GC---UCC--U-----AGAGGA-------------GC-------

S. typhimurium     UUGACAUCCACAGAACUUUCCAGAGAUGGUGCCUUCGGGAACUGUGAGAC
probe 755          GGTGTCTTGAAAGGTCTCTAACCACGGAAGC-5'

S. arizona RF908   UUGACAUCCACAGAAGUUUGCAGAGAUGCGAAUGCCUUCGGGAACUGUGAGAC
probe 754          GGTGTCTTCAAACGTCTCTACGCTTACACGGAAGC-5'
```

```
                         524                                                         569
                          |                                                           |
E. coli     - 5'- GUACAAGCAGUGGGAGCAC.GCUU.AGGCCUGUGACUGCCGUACCUUUU
Styphimu      5'- ------------------------AG---U-CCU-------------U
Sarizona      5'- ------------------------------UGAG--UUCUCA------U Pattern 1  -Styphimu  5'- GUACAAGCAGUGGGAGCACAGGUUACCUGUGACUGCGUACCUUUU
           probe849                  TCGTCACCCTCGTGTCCAAATGGACACA-5'
           probe848                    CGTGTCCAAATGGACACACTGACCATG-5'
           probe892                      CACCCTCGTGTCCAAATGGACACACTGA-5'

Pattern 2  -Sarizona  5'- GUACAAGCAGUGGGAGCAUGAGUUUUCUCAUGUGACUGCGNNCCUUUU
           probe893                  CACCCTGCTACTCAAAAGAGTACACTGA-5'
           probe894                 TCGTCACCCTCGTACTCAAAAGAGTACA-5'
           probe895                   CGTACTCAAAAGAGTACACTGACCCATG-5'
```

FIG. 9

PREDICTED HYBRIDIZATION USING VARIOUS DUAL PROBE STRATEGIES

| EXAMPLE TEST ORGANISMS | | HYBRIDIZATION OF INDIVIDUAL PROBES | | | 1 A-capture/ G-detection | 2 (A+B)-capture/ G-detection | 3 A-capture/ B-detection |
|---|---|---|---|---|---|---|---|
| | | A | B | G | | | |
| SALMONELLA | S1 | + | + | + | + | + | + |
| " | S2 | + | − | + | + | + | − |
| " | S3 | − | + | + | − | + | − |
| " | S4 | − | − | + | − | − | − |
| NON-SALMONELLA | N6 | + | + | + | + | + | + |
| " | N7 | + | − | + | + | + | − |
| " | N8 | − | + | + | − | + | − |
| " | N9 | − | − | + | − | − | − |

FIG. 10-1

| STRAIN | TARGET MOLECULE | 16S rRNA | | | | | 23S rRNA | | | | | 411 & 800 Capture/ 414 & 791 Detection |
|---|---|---|---|---|---|---|---|---|---|---|---|---|
| | TARGET REGION | 440-494 | | 990-1050 | | | 520-570 | 1470-1520 | | 1710-1748 | | |
| | PROBE | 676 | 678 | 784 | 754 | 755 | 849 | 414 | 791 | 411 | 800 | |
| e23566 | Sa. typhimurium | ++++ | - | - | - | +++ | - | ++++ | - | ++++ | - | ++++ |
| N99 | E. coli | - | - | - | - | + | - | - | ++++ | - | - | - |
| 111(lac+) | E. coli | - | - | - | - | +++ | - | - | ++++ | - | - | - |
| IG978 | E. coli | - | - | - | + | - | - | - | ++++ | - | - | - |
| IG981 | E. coli | - | - | - | - | - | - | - | ++++ | - | - | - |
| RF970 | Sh. dysenteriae | - | - | - | + | - | - | - | ++++ | - | - | - |
| RF973 | Sh. flexneri | - | - | - | - | - | - | - | ++++ | - | - | - |
| RF971 | Sh. boydii | - | - | - | ++ | ++ | - | - | ++++ | - | - | - |
| RF974 | Sh. boydii C13 | - | - | - | + | - | - | - | ++++ | - | - | - |
| IG3231 | Sh. boydii C10 | - | - | - | - | - | - | - | ++++ | - | - | - |
| IG977 | Sh. sonnei | - | - | - | - | - | - | - | ++++ | - | - | - |
| S118A | C. freundii | +++ | - | - | - | ++ | - | - | - | + | - | - |
| S103B | C. freundii | +++ | - | - | ++ | - | - | - | - | ++ | - | - |
| S135 | C. freundii | +++ | - | - | - | ++ | - | - | - | ++ | - | - |
| 621-64 | C. freundii | +++ | - | - | - | - | - | - | - | ++ | - | - |
| 460-01 | C. freundii | +++ | - | - | ++ | ++ | - | - | - | + | - | - |
| IG3209 | C. freundii | - | - | - | - | - | - | - | - | + | - | - |
| IG3210 | C. freundii | - | - | - | - | - | - | - | - | + | - | - |
| S122B | C. diversus | - | - | - | - | + | - | - | - | + | - | - |
| 3613-63 | C. diversus | - | - | + | - | - | - | - | + | - | - | + |
| 9020-77 | C. amalonaticus | - | - | - | - | - | - | ++ | - | - | ++++ | - |
| IG3217 | C. amalonaticus | - | - | - | - | - | - | +++ | - | - | ++++ | - |
| IG3218 | C. amalonaticus | - | - | - | - | - | - | +++ | - | - | +++ | +/- |
| S121B | E. agglomerans | - | - | - | - | +++ | - | - | - | - | - | - |
| PB | E. agglomerans | - | - | - | - | - | - | +++ | - | - | - | - |

FIG. 10-2

| | | 16S rRNA | | | | 23S rRNA | | | | 411 & 800 Capture/ 414 & 791 Detection |
|---|---|---|---|---|---|---|---|---|---|---|
| TARGET MOLECULE | | | | | | | | | | |
| TARGET REGION | 440-494 | | | 990-1050 | | 520-570 | 1470-1520 | | 1710-1748 | |
| STRAIN / PROBE | 676 | 678 | 784 | 754 | 755 | 849 | 414 | 791 | 411 | 800 |
| IG3200  E. agglomerans | - | - | - | - | - | - | - | - | - | - | - |
| IG3201  E. agglomerans | - | - | - | - | +++ | - | +++ | - | - | - | - |
| IG3202  E. agglomerans | - | - | - | - | - | - | - | - | - | - | - |
| IG3203  E. agglomerans | - | - | - | - | +++ | - | +++ | - | - | - | - |
| IG3204  E. agglomerans | - | - | - | - | - | - | - | - | - | - | - |
| IG3205  E. agglomerans | - | - | + | - | - | - | ++ | - | - | - | - |
| IG3206  E. agglomerans | - | - | - | - | - | - | - | - | - | - | - |
| IG3221  E. agglomerans | - | - | - | - | - | - | - | - | - | - | - |
| IG3222  E. agglomerans | - | - | - | - | - | - | - | +++ | - | - | - |
| IG3223  E. agglomerans | - | - | - | - | - | - | - | - | - | - | - |
| IG3207  E. agglomerans biogrp3 | - | - | - | - | - | - | - | - | - | - | - |
| S134  E. cloacae | - | - | - | - | +++ | - | - | - | - | - | - |
| S121A  E. cloacae | + | - | + | - | ++ | - | - | - | - | - | - |
| 57  E. cloacae | +++ | - | + | - | +++ | - | - | - | - | - | - |
| 124(lt.pnk)  E. cloacae | +++ | - | + | - | +++ | - | - | - | - | - | - |
| 126(lac+)  E. cloacae | +++ | - | + | - | +++ | - | - | - | - | - | - |
| IG3214  E. cloacae | - | - | - | - | +++ | - | - | - | - | - | - |
| IG3225  E. cloacae | - | - | - | - | + | - | - | - | - | - | - |
| S123A  E. aerogenes | - | - | - | - | - | - | - | - | - | - | - |
| IG3220  E. aerogenes | - | - | - | - | - | - | - | - | - | - | - |
| IG3227  E. aerogenes | - | - | - | - | - | - | - | - | - | - | - |
| IG3213  E. intermedium | - | - | - | - | - | - | - | - | - | - | - |
| IG3215  E. amnigenus | - | - | - | - | - | - | - | - | - | - | - |
| wheat  E. sakazakii | ++ | - | - | - | - | - | - | ++ | - | + | - |
| IG3216  E. sakazakii | +++ | - | - | - | - | - | - | +++ | - | - | - |
| wheat  E. sp. CDC19 | - | - | + | - | +++ | - | - | - | - | - | - |

FIG. 10-3

| | | TARGET MOLECULE | 16S rRNA | | | | | 23S rRNA | | | | | |
|---|---|---|---|---|---|---|---|---|---|---|---|---|---|
| | | TARGET REGION | 440-494 | | | 990-1050 | | 520-570 | 1470-1520 | | 1710-1748 | | 411 & 800 Capture/ 414 & 791 Detection |
| STRAIN | | PROBE | 676 | 678 | 784 | 754 | 755 | 849 | 414 | 791 | 411 | 800 | |
| IG3219 | E. gergoviae | | – | – | – | – | – | – | – | – | – | – | – |
| IG3230 | E. taylorae | | – | + | – | – | – | – | – | – | – | – | – |
| IG3233 | K. pneumoniae | | – | – | – | – | +++ | – | – | ++++ | – | – | – |
| IG3235 | K. pneumoniae | | – | – | – | – | +++ | – | – | +++ | – | – | – |
| IG3236 | K. oxytoca | | – | – | – | – | – | – | – | – | – | – | – |
| IG3211 | K. planticola | | – | – | – | – | – | – | – | – | – | – | – |
| IG3212 | K. terrigena | | – | – | – | – | – | – | – | – | – | – | – |
| IG3232 | K. ozaenae | | – | – | – | – | ++++ | – | – | ++++ | – | – | – |
| IG3226 | P. mirabilis | | – | – | – | – | – | – | – | – | – | – | – |
| IG3229 | P. mirabilis | | – | – | – | – | +++ | – | – | – | – | – | – |
| IG3234 | P. mirabilis | | – | – | – | – | – | – | – | – | – | – | – |
| S118B | P. vulgaris | | – | – | – | – | – | – | – | – | – | – | – |
| S133 | P. vulgaris | | – | – | – | – | – | – | – | – | – | – | – |
| RF969 | H. alvei | | – | – | – | – | – | – | – | + | – | – | – |
| 132(lac-) | H. alvei | | – | – | – | – | – | – | – | – | – | – | – |
| RF953 | Y. enterocolitica D255 | | – | – | – | – | – | – | – | – | – | – | – |
| RF954 | Y. enterocolitica I625 | | – | – | – | – | – | – | – | – | – | – | – |
| RF955 | Y. enterocolitica C200 | | – | – | – | – | – | – | – | – | – | – | – |
| RF972 | Ser. marcescens | | – | – | – | – | ++++ | – | – | ++++ | – | – | – |
| 83(mauve) | Ser. odorifera | | – | – | – | – | +++ | – | – | – | – | – | – |
| 106(lac-) | Ser. sp. | | – | – | – | – | +++ | – | – | – | – | – | – |
| S107 | Ps. sp. | | – | – | – | – | ++++ | – | – | – | – | – | – |
| 47-24(lac-) | M. morganii | | – | – | – | – | – | – | – | + | – | – | – |
| 134(lac-) | M. morganii | | – | – | – | – | – | – | – | ++ | – | – | – |
| IG3228 | A. putrefaciens | | – | – | – | – | – | – | – | – | – | – | – |

DETECTION OF SALMONELLA

This is a continuation application of U.S. Ser. No. 07/870,804, filed Apr. 17, 1992, now U.S. Pat. No. 5,495,008, which in turn is a continuation of U.S. Ser. No. 07/127,484, filed Dec. 1, 1987, now abandoned.

BACKGROUND OF THE INVENTION

This invention relates to detecting bacteria belonging to the genus Salmonella. (The term "Salmonella," as used herein, refers to the bacteria classified as such in Bergey's Manual of Systematic Bacteriology, infra). Detection of Salmonella bacteria is important in various medical and public health contexts. From the standpoint of human disease, Salmonella species are one of the most important bacteria. Salmonella bacteria can cause a variety of infections ranging from simple gastroenteritis to more severe illnesses.

According to a standard laboratory method, the presence of Salmonella in clinical specimens (e.g., stool) is detected by culturing an appropriately prepared sample on microbiological media under conditions favorable for growth of these organisms. The resulting colonies are examined for morphological and biochemical characteristics, a process that typically is started 48 hours after acquisition of the sample and takes several days to complete.

Taber et al., U.S. Pat. No. 4,689,295, discloses the use of DNA probes specific for Salmonella DNA to detect the presence of bacteria of the genus Salmonella in food.

Kohne (1968), Biophysical Journal 8: 1104–1118, discuss one method for preparing probes to rRNA sequences.

Pace, Campbell (1971), Journal of Bacteriology 107: 543–547, discuss the homology of ribosomal ribonucleic acids from diverse bacterial species and a hybridization method for quantitating these homology levels.

Sogin, et al. (1972), Journal of Molecular Evolution 1: 173–184, discuss the theoretical and practical aspects of using primary structural characterization of different ribosomal RNA molecules for evaluating phylogenetic relationships.

Fox et al. (1977), International Journal of Systematic Bacteriology 27: 44–57, discuss the comparative cataloging (of 16S ribosomal RNAs) approach to prokaryotic systematics.

Kohne et al., (1983), Gen-Probe Patent Appl., describe a strategy for obtaining nucleic acid fragments for use as probes to ribosomal RNA molecules.

The present invention will be better understood in light of the following definitions:

DNA—an abbreviation for deoxyribonucleic acid, the type of nucleic acid containing deoxyribose as the sugar component and considered to be the repository of hereditary charcteristics; i.e., the genetic material of which genes are composed.

RNA—an abbreviation for ribonucleic acid, the type of nucleic acid containing ribose as the sugar component and which, most generally, is transcribed (copied) from DNA. RNA molecules may serve informational (e.g., messenger RNA), catalytic (e.g. RNase P), or structural (e.g., ribosomal RNA, see below) cellular functions.

rRNA—Ribosomal RNA (rRNA) molecules are key elements of ribosomes, complex protein and RNA-containing "organelles" which, together with transfer RNAs, comprise the translation apparatus. Ribosomes are of profound importance to all organisms because they serve as the only known means of translating genetic information into cellular proteins, the main structural and catalytic elements of life. A clear manifestation of this importance is the observation that all cells have ribosomes.

Ribosomes contain three distinct RNA molecules which, in E. coli, are referred to as 5S, 16S and 23S rRNAs. These names historically are related to the size of the RNA molecules, as determined by sedimentation rate. However, they actually vary substantially in size between organisms. 5S, 16S, and 23S rRNA are commonly used as generic names for the homologous RNA molecules in any bacteria, and will be so used here. The evolutionary homologs of these three RNA molecules are present in the ribosomes of all organisms. In eukaryotes, the homologous RNAs are designated 5S, 18S, and 28S rRNA, respectively. Eukaryotes contain, in addition, a fourth rRNA species named 5.8S rRNA whose structural and, presumably, functional homolog is found at the 5' end of bacterial 23S rRNA.

Hybridization—the process by which, under defined reaction conditions, two partially or completely complementary nucleic acids are allowed to come together in an antiparallel fashion and form specific and stable hydrogen bonds. The stringency of a particular set of hybridization conditions is defined by the base composition of the probe/target duplex, as well as by the level and geometry of mispairing between the two nucleic acids. Stringency may also be governed by such reaction parameters as the concentration and type of ionic species present in the hybridization solution, the types and concentrations of denaturing agents present, and/or the temperature of hybridization.

Probe(s)—synthetic or biologically produced nucleic acids (DNA or RNA) which, by design or selection, contain specific nucleotide sequences that allow them to hybridize, under defined stringencies, specifically (i.e., preferentially) to target nucleic acid sequences.

Target molecule—a nucleic acid molecule to which a particular probe is capable of preferentially hybridizing.

Target sequence—a nucleic acid sequence within the target molecules to which a particular probe is capable of preferentially hybridizing.

Salmonella-specific sequences—nucleotide sequences within a target molecule which exhibit significant sequence differences between Salmonella and non-Salmonella enteric bacteria.

Other definitions are given as their first use arises in the text.

SUMMARY OF THE INVENTION

The present invention features nucleic acid probes or probe sets consisting essentially of DNA or RNA sequences which are capable, under specific hybridizing conditions, of detecting the presence of ribosomal RNA (rRNA) molecules of Salmonella bacteria and are not capable, under the same conditions, of detecting the rRNA of non-Salmonella bacteria which may be present in the test sample.

The present invention also features an assay system for the utilization of said probes, the format of which can enhance the aforementioned desirable behavior of the probes. The invention exhibits the following enhanced performance capabilities:

a) increased sensitivity; i.e., the ability to detect fewer Salmonella in any given sample than presently available methods, b) potentially significant cost reductions in probe production due to the use of chemically, rather than biologically, synthesized probes, and c) accurate identification of even biochemically unusual Salmonella, because of the rRNA sequence characterizations which provide the basis of such identification.

The use of Salmonella RRNA as target molecules provides a number of advantages, among them:

1) The rRNAs constitute a significant component of cellular mass. Although estimates of cellular ribosome content vary, actively growing Salmonella bacteria may contain upwards of $5.0 \times 10^4$ ribosomes per cell, and therefore $5.0 \times 10^4$ copies of each of the rRNAs (present in a 1:1:1 stoichiometry in ribosomes). In contrast, most other potential cellular target molecules, genes or RNA transcripts thereof, are present in much lower abundance.

(2) The rRNAs (and the genes encoding them) appear not to be subject to lateral transfer between contemporary organisms. Thus, rRNA primary structure provides an organism-specific molecular target, rather than a gene-specific target as would likely be the case, for example, of a plasmid-borne gene or product thereof which may be subject to lateral transmission between contemporary organisms.

In addition to providing the advantages inherent in rRNA detection, above, the present invention provides probes to Salmonella rRNA target sequences which are sufficiently similar in a significant number of Salmonella that one or a few probes can hybridize to the target region in those Salmonella, and are sufficiently different in most or all non-Salmonella rRNAs that, under some conditions where the probe(s) hybridize to Salmonella rRNAs, they are not capable of hybridizing, or hybridize very poorly, to most non-Salmonella rRNAs. These probe characteristics are defined as inclusivity and exclusivity, respectively.

As described in detail below, the true situation is considerably more complex than simply defining a probe (or set of probes) which hybridize to all Salmonella and not non-Salmonella bacteria. A number of probes are described which specifically hybridize to certain interesting and useful subsets of Salmonella; other probes are described which, while individually exhibiting rather poor exclusivity properties, are nevertheless valuable components of probe sets which, when combined in an appropriate assay system, exhibit desirable overall performance characteristics. In one of the novel assay formats described below (dual-specific, capture/detection oligos), the ideal requirement for 100% exclusivity of each probe may be relaxed without sacrificing overall exclusivity behavior of the probe set, if individual probes of the set have non-overlapping patterns of undesirable cross hybridization.

In addition, the probes of the invention hybridize to target regions which can be rendered accessible to the probes under normal assay conditions.

Other features and advantages of the invention will be apparent from the following description of the preferred embodiments thereof, and from the claims.

DESCRIPTION OF THE PREFERRED EMBODIMENTS

Preferred embodiments of the invention are now described, after first briefly describing the drawings.

BRIEF DESCRIPTION OF THE DRAWINGS

FIGS. 3-1 and 3-2 show the nucleotide sequence of the about 1405–1597 region of FIG. 1, including the sequence of certain relevant bacterial strains and probes corresponding to portions of that region.
FIG. 3-1: Secondary structure of *S. typimurium* 23S rRNA through this target region.
FIG. 3-2: Salmonella probes to this region are shown aligned below their target sequences in two Salmonella 23S rRNAs representing the two distinct sequence patterns so far observed through this region. The corresponding sequence observed from one significant "competitor" organism, an *Enterobacter agglomerans* isolate from peanut butter (Eagg1 PB) also is shown. Position numbers correspond to the *E. coli* numbering system. Only those positions which are different from *E. coli* are shown. Symbols used are: (.) deletion with respect to other sequences in the alignment, (−) same nucleotide as appears in *E. coli*. Lower case "a", or "g" letters indicate non-complementary bases, lower case "c" indicates a cytosine analog capable of accepting a biotin label, and lower case "t" indicates a thymine positioned 5' from a "c" in order to enable later addition of the "c".

FIGS. 4-1 and 4-2 show the nucleotide sequence of the about 1700–1760 region of FIG. 1, including the sequences of certain relevant bacterial strains and probes corresponding to portions of that region. FIG. 4-1: Secondary structure of *E. coli* 23S rRNA through this target region. Differences with the *S. arizona* and *S. typhimurium* (circled) sequences are indicated. FIG. 4-2: Salmonella probes to this region are shown aligned below their target sequences in three Salmonella 23S rRNAs representing the three sequence patterns so far observed through this region. Position numbering and symbols are as in FIGS. 3-1 and 3-2.

FIGS. 5-1 and 5-2 show the nucleotide sequence of the about 430–510 region of FIG. 2, including the sequences of certain relevant bacterial strains corresponding to portions of that region. FIG. 5-1: Secondary structure of *E. coli* 16S rRNA through this target region. Differences with the *S. arizona* and *S. typhimurium* (circled) sequences are indicated. FIG. 5-2: Salmonella probes to this region are shown aligned below their target sequences in four 23S rRNAs representing four of the sequence patterns so far observed through this region. Position numbering and symbols are as in FIGS. 3-1 and 3-2.

FIGS. 6-1 and 6-2 show the nucleotide sequence of the about 991–1045 region of FIG. 2, including the sequences of certain relevant bacterial strains corresponding to portions of that region. FIG. 6-1: Secondary structure of *E. coli* 16S rRNA through this target region. FIG. 6-2: Salmonella probes to this region are shown aligned below their target sequences. *E. coli* position numbering is used.

FIGS. 7-1 and 7-2 show the nucleotide sequence of the about 512–580 region of FIG. 1, including the sequences of certain relevant bacterial strains corresponding to portions of that region. FIG. 7-1: Secondary structure of *E. coli* 23S rRNA through a portion of this target region. FIG. 7-2: Salmonella probes to this region are shown aligned below their target sequences. Numbering and symbols are as in FIGS. 3-1 and 3-2.

FIG. 9 is an illustration of various alternative outcomes possible using either the dual (specific/generic), or dual specific capture/detection probe format. Referring to FIG. 8, strategy 1 corresponds to lines 2 or 8, strategy 3 corresponds to lines 1 or 7. Strategy 2 corresponds to the concept of adding multiple Salmonella-specific capture probes to a "set" in order to achieve the required inclusivity.

FIGS. 10-1, 10-2 and 10-3 are a tabulation of representative dot blot hybridization results which demonstrates the exclusivity behavior of certain of the probes described herein.

Probe Development Strategy

Figure 1:
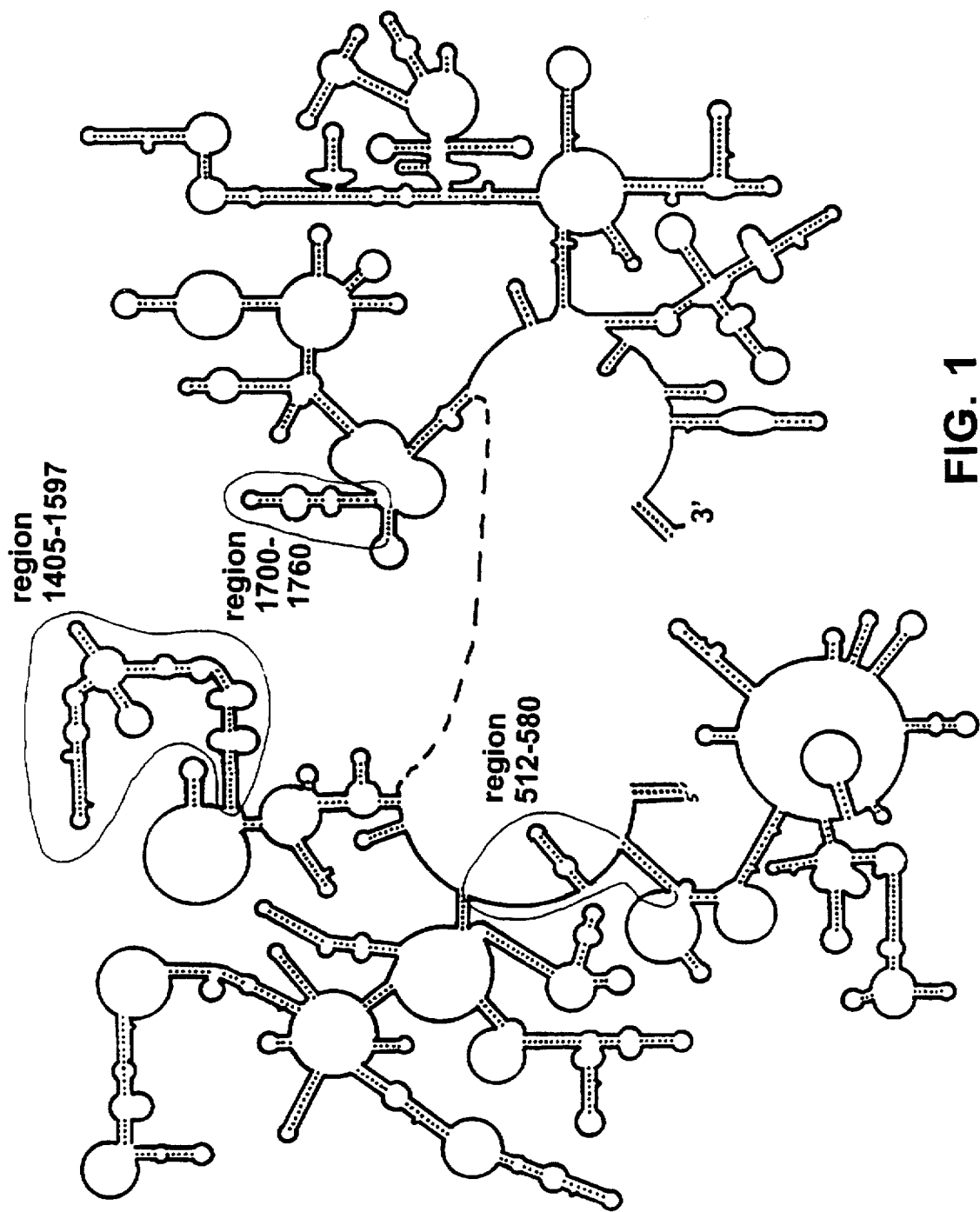
FIG. 1 is a diagrammatic illustration of *E. coli* 23S rRNA.

The first step in the development of probes of the invention is to identify regions of 16S and 23S rRNA which potentially can serve as target sites for Salmonella-specific nucleic acid probes. As a practical matter, it is difficult to predict, a priori, which non-Salmonella organisms might be present in any test sample. Because of the large number of such potential non-Salmonella bacteria, demonstrating exclusivity for any given probe sequence is extremely difficult and laborious. However, a more rigorous criterion can be adopted which obviates the need to know, during initial stages of research and development, what non-Salmonella bacteria might be present in all test samples that ultimately will be screened using the probe. This entails a knowledge of the phylogenetic relationships among Salmonella and between Salmonella and other groups of bacteria. Specifically, it is taken as an operating hypothesis that the exclusivity criterion may be satisfied by determining that a particular target region in Salmonella rRNA is sufficiently different from the homologous region in the rRNA of representative close evolutionary relatives of Salmonella that the Salmonella and relatives can be distinguished by hybridization using a probe specific to the Salmonella sequence. As a general rule then, based on phylogenetic principles, the RRNA sequences of more distantly related organisms, even though their actual identity is not necessarily known, can be predicted to be at least as different, in a particular region of sequence, than the aforementioned close evolutionary relative of Salmonella.

Although this principle has been adequately demonstrated over spans of fairly large evolutionary distance (e.g. interphylum level), it has not been demonstrated over the close distances under investigation here. In fact, we have found that while, on average, the principle holds quite well for the Salmonella and close relatives, it also is observed that instances of random sequence variation in the target regions occasionally and unpredictably violate the principle. Therefore, experimental testing of probes against large panels of representative Salmonella and non-Salmonella bacteria must remain the final criterion of probe performance.

As our first step in identifying regions of Salmonella rRNA which might be useful as target sites for nucleic acid hybridization probes, we have determined nearly complete nucleotide sequences of both the 16S and 23S rRNAs from two species of Salmonella, *S. typhimurium* and *S. arizona*. These were selected as representatives of two of major Salmonella DNA homology groups, and thus are representative of the evolutionary breadth of genus Salmonella. (Six such groups have been defined altogether, but four are comprised of small collections of "atypical" Salmonella.) Nucleotide sequences of various portions of the rRNAs were determined by standard laboratory protocols either by cloning (Maniatis et al. 1982, Molecular Cloning: A laboratory manual) and sequencing (Maxam & Gilbert, 1977, Proceedings of the National Academy of Science. USA 74: 560–564, Sanger et al. 1977, Proceedings of the National Academy of Science. USA 74: 5463–5467) the genes which specify the rRNAs, and/or by direct sequencing of the rRNAs themselves using reverse transcriptase (Lane et al. 1985, Proceedings of the National Academy of Science. USA 82: 6955–6959). The derived nucleotide sequences were compared to one another and to other available rRNA nucleotide sequences, in particular, to those of the closely related enteric bacterium *Escherichia coli*. A number of regions of sequence were discovered that exhibit potentially useful exclusivity characteristics with respect to the *E. coli* rRNA sequences (i.e., contain Salmonella-specific sequences). These are disclosed below.

As discussed above, this preliminary analysis provides only a demonstration of feasibility. Further experimental testing of each nucleic acid probe is required to rigorously demonstrate the desirable characteristics discussed above, namely: 1) adequate exclusivity as to most or all closely related organisms, 2) useful inclusivity patterns with respect to Salmonella, and 3) accessibility of the target regions under various assay conditions that might actually be employed. Because of the extremely large number of organisms potentially relevant to defining exclusivity (presently ca. 22 enteric genera, comprised of some 69 species and 29 unspeciated "biogroups", Farmer et al. 1985, Journal of Clinical Microbiology 21: 46–76) and inclusivity (on the order of 2000 species and serotypes of Salmonella) characteristics of test probes, we have adopted the herein described interactive strategy with respect to testing and refinement of potential probes.

The first generation probes are designed based on the principle of maximizing utilization of the observed nucleotide sequence variation in the target regions of Salmonella and non-Salmonella bacteria. There is then carried out preliminary testing of the inclusivity and exclusivity properties of the first generation probes by "dot blot" analysis. Dot blot analysis can be performed in many different ways, but generally involves immobilizing a nucleic acid or a population of nucleic acids on a filter (e.g., nitrocellulose, nylon, or other derivatized membranes which are commercially available and useful for this purpose). RNA can easily be so immobilized and then probed under any of a variety of nucleic acid hybridization conditions (i.e., stringencies), for nucleotide sequences of interest. Techniques are also available in which RNA present in crude (unpurified) cell lysates can be immobilized without having to first purify the nucleic acid in question. This latter approach significantly decreases the amount of effort required to screen for particular nucleotide sequences which may be present in the nucleic acids of any particular organism and, moreover, is amenable to the mass screening of large numbers of organisms. It, therefore, is the method of choice for testing the exclusivity and inclusivity properties of potential nucleic acid hybridization probes versus large numbers of organisms.

A list of non-Salmonella, enteric bacteria which exemplify the type of bacteria that may be present in potentially Salmonella-containing samples is given in Table 1. These also represent many of the genera most closely related to Salmonella. As discussed above, a probe which demonstrates good exclusivity characteristics to such a broad representation of enteric Salmonella relatives can reasonably be predicted to behave similarly to a much broader list of enteric organisms than actually tested.

TABLE 1

Partial Listing of Non-Salmonella Enteric Bacteria Used in Screening Potential Probes

| | |
|---|---|
| *Escherichia coli* | *Klebsiella ozaenae* |
| *Enterobacter cloacae* | *Klebsiella planticola* |
| *Enterobacter agglomerans* | *Klebsiella terrigena* |
| *Enterobacter gergoviae* | *Providencia rettgeri* |

TABLE 1-continued

Partial Listing of Non-Salmonella Enteric Bacteria
Used in Screening Potential Probes

| | |
|---|---|
| Enterobacter aerogenes | Proteus mirablis |
| Enterobacter amnigenus | Pseudomonas aeruginosa |
| Enterobacter intermedium | Serratia odorifera |
| Enterobacter sakazakii | Seratia liquefaciens |
| Enterobacter taylorae | Serratia marcescens |
| Citrobacter freundii | Shigella flexneri |
| Citrobacter diversus | Shigella sonneii |
| Citrobacter amalonacticus | Shigella boydii |
| Hafnia alvei | Shigella boydii C-13 |
| Klebsiella pneumoniae | Shigella dysenteriae |
| Morganella oxytoca | Yersinia enterocolitica |
| Proteus vulgaris | Alteromonas putrefaciens |

An analogous listing. comprised of Salmonella bacteria for which it is highly desirable that any Salmonella-specific probe be inclusive, would be very much longer than the "exclusivity panel" listing given in Table 1. Although DNA/ DNA hybridization data suggest the existence a number of intra-genic groupings of Salmonella species and serotypes, many strains, particularly newly described ones, cannot be assigned with certainty to one of these groupings without resorting to DNA/DNA hybridization analysis. Our Salmonella reference collection presently contains some 345 strains, representing all major and minor phylogenetic, biochemical, and serological groupings as well as a number of taxonomically undefined Salmonella. Inclusivity behavior of all potentially useful probes (or sets of probes) is characterized with respect to this collection.

The next step in probe design is sequence analysis of undesirable (false) positives and missed Salmonella (false negatives). The inclusivity and exclusivity information gathered from initial dot blot screenings of each probe sometimes identifies Salmonella strains to which the test probe hybridizes only weakly or not at all, and non-Salmonella strains to which it does hybridize. Rather than randomly modifying and retesting new versions of a given probe, a more informative approach has been adopted in which the relevant nucleotide sequence underlying the undesirable hybridization behavior in the organisms in question is determined. For this purpose, a reverse transcriptase sequencing strategy (Lane et al., 1985; Qu et al., 1983, Nucleic Acids Research II: 5903–5920) is employed, which makes use of sequencing primers which have been specifically designed to provide direct access to the rRNA regions of interest.

The next step is the refinement of probe geometries and retesting. Using the information gathered in the sequencing analysis above, new probes of altered geometries with respect to the target region (e.g., complementary to slightly different nucleotide sequences within the target region), and/or altered nucleotide sequence (but targeted at the same target sequences, for instance), are designed and synthesized. These are then retested either by the dot blot procedure described above and/or by various other means such as one of the solution hybridization assays described below. Strict complementarity between the probe sequence and the target sequence is not necessarily the primary criterion for probe design. More important are satisfactory inclusivity and exclusivity properties.

Several other considerations also affect optimal design characteristics of a probe sequence. The first is consideration of the geometry of the probe with respect to itself. We have found that potentially useful target regions of the 16S and 23S rRNAs often are located in regions that exhibit substantial potential for self complementarity. Therefore, probes to these regions can also exhibit self complementarity. Because potential interactions between the probe and target sequences are governed by the same types of interactions that govern the intramolecular annealing of the target or probe sequences to themselves, it is possible, particularly under solution hybridization conditions, that self-complementary probes can render themselves inaccessible for hybridization to their target sequences either by intra- or inter-molecular probe/probe interactions. Thus, one aspect of probe design is to minimize such self-complementarity. This often necessitates making a compromise between maximum utilization of Salmonella-specific sequences and acceptable probe geometry.

An additional consideration in probe design arises with respect to the inclusivity criterion. The preferred probe will be one which, while displaying appropriate exclusivity behavior, also can hybridize to the rRNA(s) of all desired Salmonella bacteria. Because the genus Salmonella itself is comprised of bacteria which exhibit significant phenotypic and genetic (including, as disclosed below, rRNA diversity), it may not be possible to design (or discover) such an "ideal" probe. In practice, rather than demanding a "universal" Salmonella probe, a set of Salmonella-specific probes is sought, each of which exhibits appropriate exclusivity, and some useful level of inclusivity. In aggregate, the set of probes will detect most or all Salmonella and few or no non-Salmonella bacteria. In such a set, for example, one probe can detect all but one or a few important Salmonella strains, and another probe may hybridize with good exclusivity only to those few Salmonella strains missed by the first probe. Thus, although the probes disclosed below are characterized on an individual basis with respect to inclusivity characteristics, it must be borne in mind that the concept of "sets" of specific probes detailed above must also be considered in determining the importance of individual probes.

This set notion also extends to evaluation of the exclusivity behavior of individual probes. For example, in the dual-specific capture/detection format described below, undesirable hybridization to non-Salmonella bacteria by otherwise useful probes or probe sets can be reduced or abolished by manipulation of the composition of the probe set(s) and the assay strategy employed.

A corollary of the "set notion of genus-level, Salmonella-specific probes is that certain aspects of the design of individual probes may reflect the requirement that their behavior be compatible, under particular assay conditions, with the "behavior" of other probes in the set. An additional set of constraints on probe design are created where the probes are to be used in a solution hybridization format. For a variety of applications, solution hybridization formats can be the preferred choice of assay design. Potential advantages of solution hybridization assays include: a) enhanced kinetic properties of hybridization with respect to solid phase hybridizations (e.g., dot blot analyses, as outlined above), b) potentially enhanced background reduction characteristics of the assay (detection) system, and c) enhanced end-user "friendliness" of the assay system test.

Solution hybridization assays raise the issue of accessibility of the target region to probes of various geometries. The strength of probe/target region interactions in solution hybridization can be controlled, to a certain extent, by varying parameters such as probe length, extent of complementarity to the target region, self-complementarity, positioning of the target-sequence-complementary positions within the probe, incorporation of novel (e.g., derivatized) nucleotides, incorporation of various non-standard (i.e., non-Watson/Crick type) base pairings between the probe and target sequence (e.g., quanosine-uridine, adenosine-guanosine, or inosine-cytosine base pairs), etc.

The strength of particular probe/target interactions can also be influenced by assay conditions. For example, in addition to those assay parameters mentioned above, selective deproteinization of the rRNA target, selective ribonuclease treatment of the rRNA target, selective use of second-site (not necessarily Salmonella-specific) probes to alleviate intramolecular target/target interactions and/or to accelerate probe/target interactions, and selective use of second-site probes in dual-probe capture/detection strategies (see below), can all improve assay results.

In practice, the analysis of probe behavior under liquid hybridization conditions is not necessarily a discrete step, as implied here for clarity of presentation but, rather, is approached in an integrated fashion throughout the process of probe development.

The final step of probe design and analysis is testing of real (e.g., food/clinical) samples.

The probes of the invention can be used in a variety of formats, some of which are discussed below.

Antibody Capture Format

1. Bacteria are lysed, in one embodiment, by treatment with low concentrations of base (e.g., NaOH).

2. After lysis, the solution is neutralized to an approximate pH of 7 with buffer containing biotinylated probe or probes, and if necessary, a sodium or potassium salt is added to approximately 0.6 Molar. In one embodiment, neutralization, salt addition, and probe addition are carried out concurrently with a concentrated solution of sodium phosphate and probe.

3. Hybridization is allowed to occur.

4. In one embodiment, the sample is then treated with a high concentration of ribonuclease and detergent at an elevated temperature, in order to degrade any probe/target complexed due to non-specific hybridization of the probe(s).

5. The solution containing the target-probe complex is now brought into contact with a surface containing purified antibody (polyclonal or monoclonal) directed against DNA/RNA hybrids. This surface can be the inside or outside of a plastic tube, a microtiter plate well, a dipstick paddle, magnetic beads or polystyrene micro or macro beads. The target-probe complex is allowed to bind to the antibody and the non-hybridized probe and non-Salmonella targets are washed away with the use of a buffered solution at room temperature.

6. A streptavidin-enzyme conjugate is added and, following incubation, excess conjugate is removed by washing.

7. A chromogenic substrate for the enzyme then is added to the plastic surface, and a solution product is formed.

8. The color developed in the tube is a function of the amount of specific target captured and is quantified using a spectrophotometer or ELISA plate reader.

Streptavidin Capture Format

1. In one embodiment, bacteria are lysed, neutralized and hybridized with a biotinylated probe or probe set as described above. Alternatively, the organisms' cell wall may be weakened by enzymatic treatment and then lysed by the addition of a chaotropic salt (e.g. guanidinium thiocyanante) and probe or probes.

2. After hybridization, in one embodiment, the sample is then treated with a high concentration of ribonuclease and detergent at an elevated temperature, in order to destroy any probe/target complex which is due to non-specific hybridization of the probe(s). This step is not used with chaotrope lysis.

3. The solution containing the target-probe complex is now brought into contact with a surface containing bound streptavidin. As in the antibody capture method, this surface can be in a variety of configurations. The target-probe complex and free probe binds to the surface via the biotin-avidin bridge, and the non-hybridized nucleic acid is removed through a series of washes.

4. The bound target-probe complex (DNA/RNA hybrid) is differentiated from the surface bound excess free probe by the addition of specific antibody directed against DNA/RNA hybrids (polyclonal or monoclonal). In one embodiment, this antibody is directly conjugated to an enzyme such as horseradish peroxidase or alkaline phosphatase.

5. If an antibody enzyme conjugate was used for binding to the DNA/RNA hybrids, substrate is then added and the bound enzyme-probe-target complex detected by the generation of colored product as described above. An unconjugated primary antibody can be detected by the addition of a second antibody-enzyme conjugate with specificity against the first antibody (e.g., goat anti-mouse horseradish peroxidase conjugate for a monoclonal) and subsequent substrate addition and colored product generation.

Homopolymer Capture-Single Probe Format

1. Bacteria are lysed by either of the two lysis procedures detailed above.

2. Hybridization is carried out with probe or probes that have been enzymatically tailed with 20–200 dA residues at the 3' end.

3. In one embodiment, a high concentration of RNAase and detergent is then added and allowed to digest any non-specifically hybridized target RNA.

4. The solution containing the target-probe complex is then brought into contact with a surface containing bound dT homopolymer 15–3000 nucleotides in length, under conditions that will allow hybridization between the dT and the dA "tail" of the probe, thus capturing the target-probe complex, as well as any remaining free probe.

5. Unhybridized nucleic acids and cellular debris are washed away, leaving the captured DNA/RNA complex attached via the dA-dT homopolymer.

6. The bound target-probe complex (DNA/RNA hybrid) is differentiated from the surface-bound excess free probe by the addition of specific antibody directed against DNA/RNA hybrids (polyclonal or monoclonal). In one embodiment, this antibody is directly conjugated to an enzyme such as horseradish peroxidase or alkaline phosphatase.

7. If an antibody enzyme conjugate was used for binding to the DNA/RNA hybrids, substrate is then added and the bound enzyme-probe-target complex detected by the generation of colored product. An unconjugated primary antibody can be detected by the addition of a second antibody-enzyme conjugate with specificity against the first antibody (e.g., goat anti-mouse horseradish peroxidase conjugate for a monoclonal) and substrate addition and colored product generation.

Homopolymer Capture—Dual Probe Format

1. Bacteria are lysed by either of the two lysis procedures detailed above.

2. Hybridization is carried out with 2 different probes, at least one of which, but not necessarily both of which, should preferentially anneal Salmonella target molecules. The capture probe or probes are enzymatically tailed with 20–200 dA residues at the 3' end, and the reporter probes (oligomeric or polymeric DNA or RNA) are labeled either chemically or enzymatically with biotin.

3. The solution containing the target-probe complex is then brought into contact with a surface containing bound dT homopolymer 15–3000 nucleotides in length, under conditions that will allow hybridization between the dT and the dA "tail" of the probe, thus capturing the target-probe complex, as well as any remaining free capture probe.

4. Unhybridized nucleic acids and cellular debris are washed away, leaving the captured DNA/RNA complex attached via the dA-dT homopolymer.

5. The bound biotinylated reporter probe is detected by the addition of a streptavidin-enzyme complex, incubation to allow specific binding, washing to remove non-bound complex, addition of substrate and subsequent color development, as described in the antibody capture section above.

Figure 8:
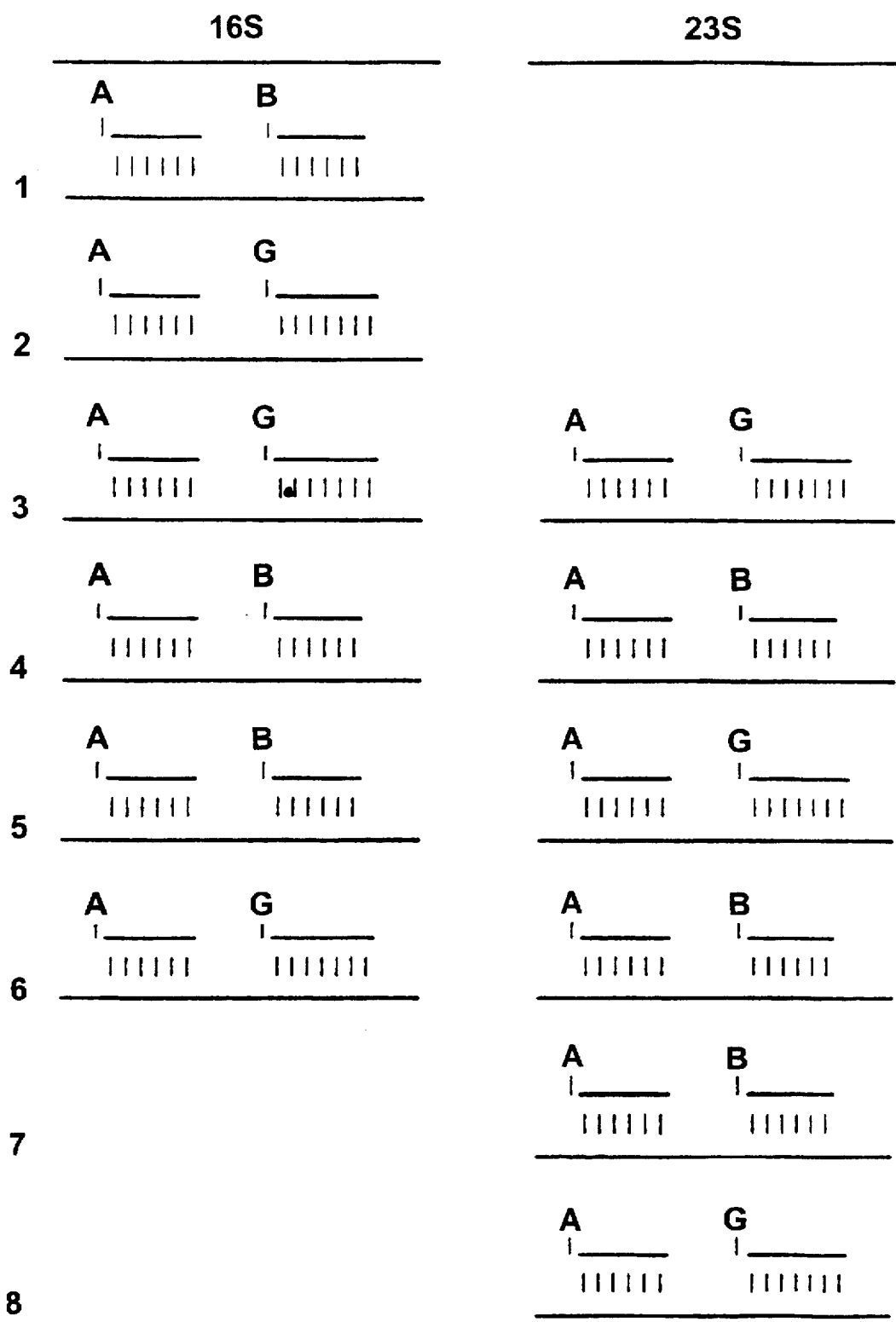
FIG. 8 is an illustration of the various types of dual probe stategies which may be utilized to capture and detect 16S and/or 23S rRNA target molecules. Two Salmonella-specific (A & B) and one nonspecific (G=generic) probes are shown. Lines 1 and 7 are the two simplest examples of the dual specific format.

Distinct consequences may derive from different versions of the dual probe format just described depending upon whether and how Salmonella-specific and non-specific probes are employed in the assay. Some of the possible variations are illustrated in FIG. 8, which emphasizes that both the 16S and 23S rRNAs (individually or together) can be subjected to dual probe (specific capture/generic detection) or dual specific (capture/detection) strategies. The fundamental differences between the illustrated combinations derive from the alternative use of specific/generic or specific/specific combinations of capture/detection probes. A consideration of the simplest case is illustrative. Compare, for example lines 1 and 2 in FIG. 8. Line 1 illustrates a specific/specific dual probe assay scheme; line 2 illustrates a specific/generic dual probe scheme.

Some of the hypothetical outcomes possible using these alternative strategies is shown in FIG. 9. The illustrated outcomes were arbitrarily chosen to reflect a near-random distribution of hybridization positives and negatives for the hypothetical Salmonella probes A and B. In actuality, the relevant distribution for many of the Salmonella-specific probes described herein is far from random. Probe G illustrates a non-specific (i.e., G=generic) detection probe which will hybridize, under normal assay conditions, to any 16S or 23S rRNA target molecule (depending upon the specificity of the Generic probe, i.e., for 16S or 23S).

Outcome 1 is based on using a single specific (capture) probe (A) and a generic detection probe (G). In essence, the outcome is defined by the inclusivity and exclusivity properties of probe A. Probe G detects everything that probe A captures.

Outcome 2 is an extension of strategy 1, and is based on the additivity of inclusivity and exlusivity properties associated with specific capture probes A and B. Note that inclusivity in case 2 is improved over that in 1, but exclusivity is worsened.

The outcome of strategy 3 (the dual specific oligo format) is conceptually different from that outlined for strategies 1 or 2. Rather than adding the inclusivity and exclusivity sets associated with probes A and B, only those organisms to which both A and B hybridize are included as positives in the dual specific oligo format. For example, the target molecule of organism N7 is captured by probe A but not detected by probe B. Conversely, the target molecule of organism N8 would be detected by probe B but, since it is not captured by A, is not available to be detected.

Strategy 3 would appear in theory to be less useful than the first two because the inclusivity and exclusivity profiles exhibit equal and offsetting "tradeoffs." However, based on our observations on the patterns of nucleotide sequence variation in the 16S and 23S rRNAs of various enteric bacteria (including Salmonella) and on the observed hybridization patterns of probes of various specificity to the different target sites, we conclude:

(1) that different potential Salmonella-specific target regions exhibit distinctly different and non-random patterns of sequence variation not only between Salmonella but also between Salmonella and various non-Salmonella bacteria.

(2) that, in particular, bacteria belonging to the genera Citrobacter and Enterobacter (to the exclusion of other enteric genera) are the most "problematic" with respect to hybridization to various otherwise quite Salmonella-specific probes, and (3) that, based on known information, including information of phylogenetic and/or biochemical character, the observed patterns of sequence variation are not fully predictable.

Probes

The probe selection strategy described above has yielded a number of probes useful in identifying Salmonella bacteria in samples. The first step in the probe selection process was to carry out nucleotide sequence analysis on the 16S and 23S rRNA's of *S. typhimurium* and *S. arizona*. Comparison of these Salmonella sequences to non-Salmonella rRNA sequences (particularly *E. coli*) identified sequences which meet the exclusivity criterion, i.e., they are essentially Salmonella specific, and are thus potential target regions to which probes could be directed. This analysis yielded five regions of rRNA (three in 23S and two in 16S) which contain useful or potentially useful Salmonella specific sequences. The positions of these regions, with respect to the positions of their structural and evolutionary homologs in *E. coli* rRNAs, are indicated by circled regions in FIG. 1 (23S rRNA) and FIG. 2 (16S rRNA). Since homologous rRNAs vary somewhat in size from organism to organism and since, in every case, the exact 5' nucleotide (by convention assigned as position number 1) of the Salmonella rRNAs have not been documented, use of the *E. coli* numbering system, as is commonly done, provides the least ambiguous designation of regions of bacterial rRNA sequences.

Figure 2:
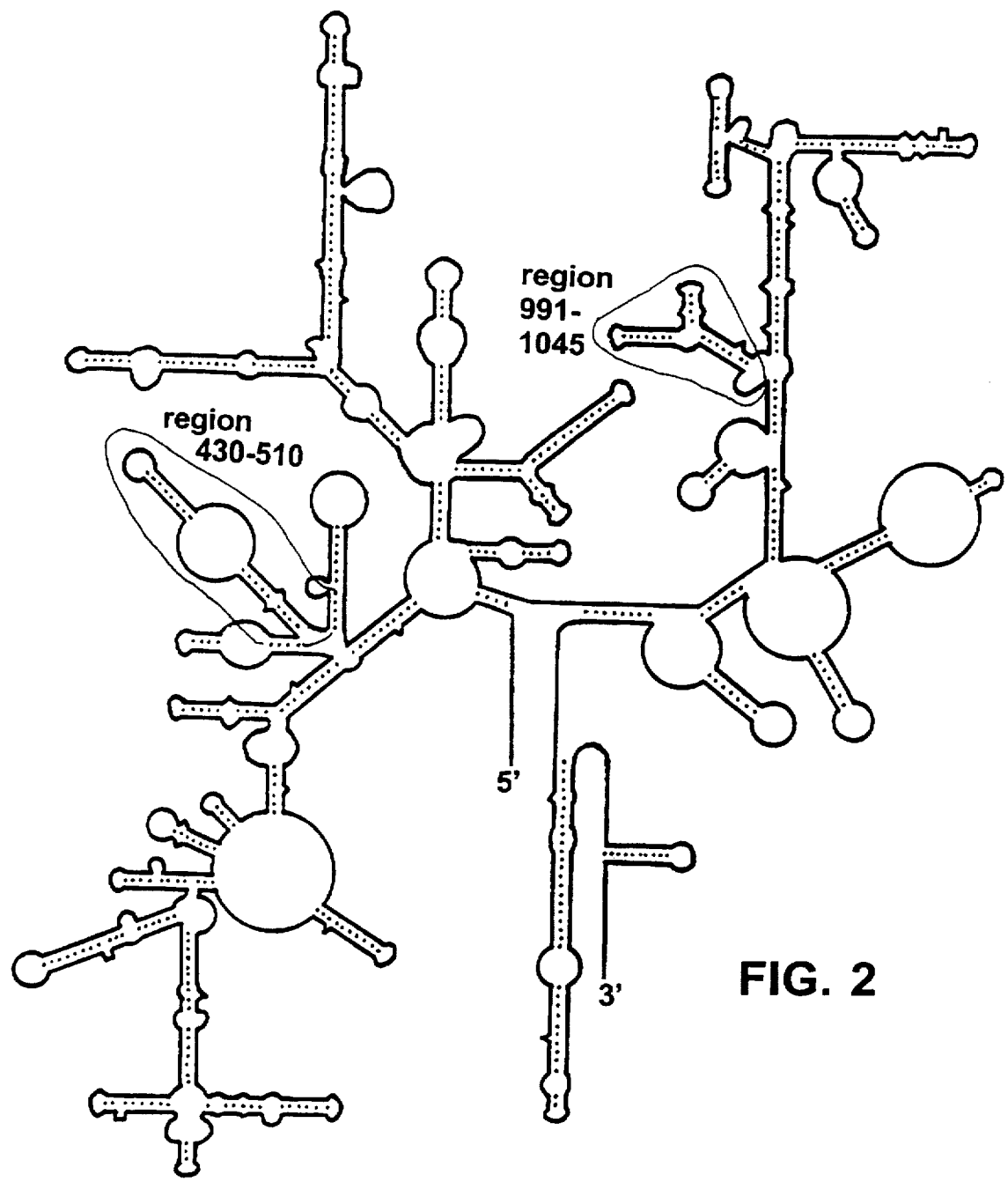
FIG. 2 is a diagrammatic illustration of *E. coli* 16S rRNA.

Referring to FIGS. 1 and 2, the definite Salmonella-specific sequences are:
1) region about 1405–1597; 23S rRNA;
2) region about 1700–1760; 23S RRNA;
3) region about 430–51.0; 16S rRNA.

Still referring to FIGS. 1 and 2, the probable Salmonella-specific sequences are:
1) region about 997–1045; 16S rRNA:
2) region about 512–580; 23S rRNA;

These Salmonella-specific regions, and related probes, are described in more detail below. Liquid hybridization assays using probes to these regions demonstrate good accessability of target sequences in these regions under both chaotropic and non chaotropic conditions. Generally, good sensitivity also is achieved. Not all probes shown in the Figures are discussed, however each probe is useful in the invention. Further, other probes may be readily constructed, using the guidelines discussed above. These examples are not limiting to this invention.

Figures 1, 3:
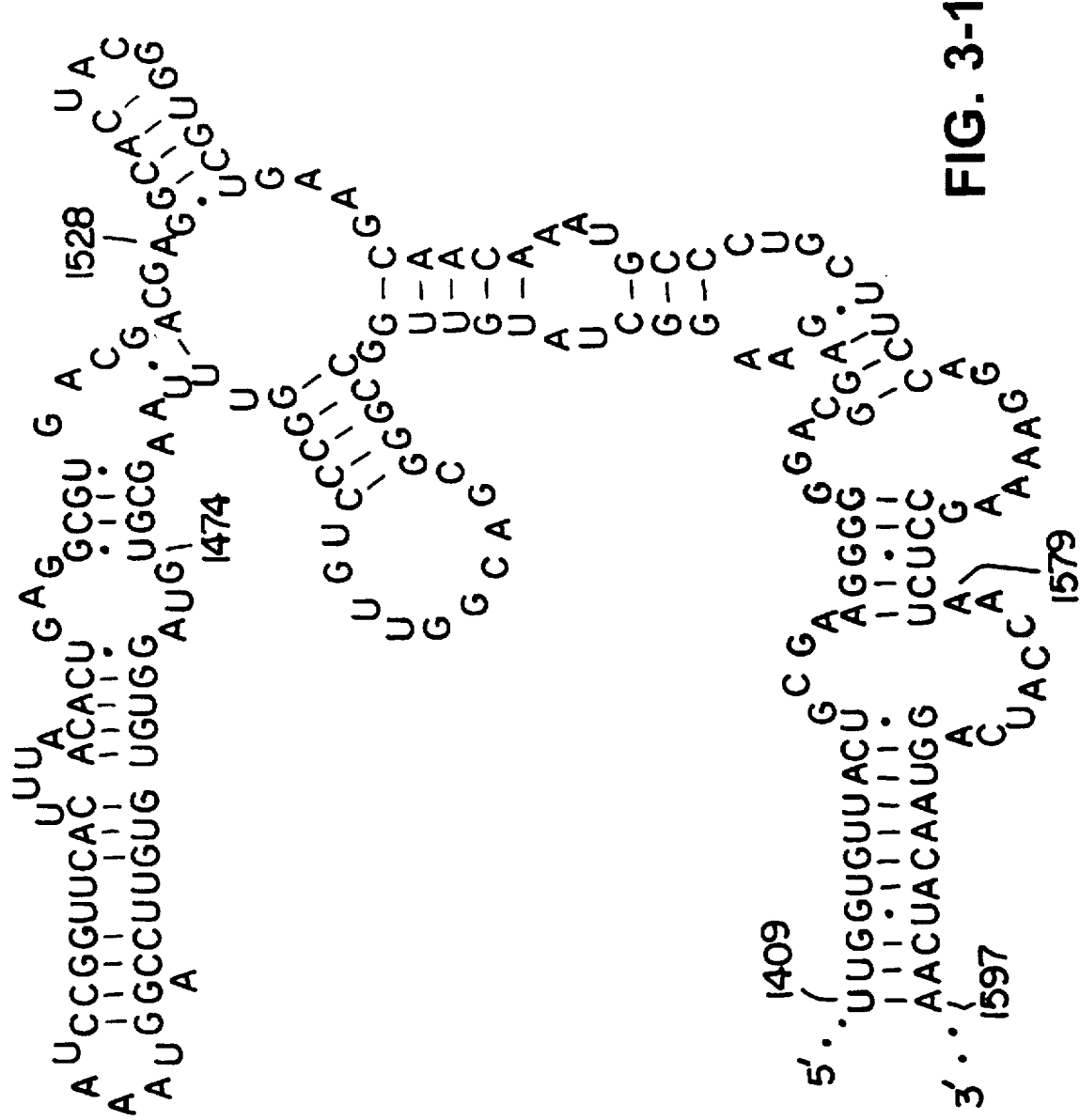

1) 23S rRNA region 1405–1597. This region is shown in FIG. 3. Of the Salmonella strains whose 23S rRNA sequences have so far been inspected through this region, two structural patterns have been observed. One of these (designated pattern 1) is identical to that observed in *E. coli*, and is therefore, by definition, not a Salmonella-specific sequence. Nevertheless, probes complementary to this sequence pattern do hybridize to certain Salmonella rRNAs in a useful and important fashion, see below. The other (designated pattern 2) is identical to that originally determined to exist in the 23S rRNA of *S. typhimurium* strain e23566 (shown in FIG. 3). Pattern 2 contains two nucleotide insertions, in addition to the indicated nucleotide sequence differences, with respect to the *E. coli* (pattern 1) sequence through this region, and can be predicted to adopt an altered secondary structure compared to pattern 1-containing rRNAs.

Referring to FIG. 3, a synthetic probe, designated "414", has a sequence complementary to a portion of the *S. typhimurium* 23S 1405-1597 region, also shown in FIG. 3. Probe 414 has been shown in dot blot analyses, using Salmonella and non-Salmonella strains, to exhibit good exlusivity characteristics, i.e., under conditions under which it hybridizes to pattern 2-containing rRNA, it fails to hybridize to the rRNA of *E. coli* or most of the other representative strains of the enteric bacterial species listed in FIG. 10. Extensive dot blot hybridization testing has revealed a number of Citrobacter and Enterobacter strains to which probe 414 will hybridize under assay or near assay conditions. (Exclusivity data is provided in FIG. 10).

The inclusivity characteristics of probe 414 were also found to be useful; the probe hybridized to the rRNA's of 91% (311/343) of Salmonella strains tested, although only 66% (27/41) of the *S. arizona* strains tested were detected by the 414 probe in dot blot hybridization assays; 94% (285/303) of non-*S. arizona* strains were detected by probe 414.

Variants of probe 414 can be designed in order to "match" the behavior characteristics of other probes of the probe sets in which probe 414 (or derivatives thereof) ultimately are utilized. Some of these are shown in FIG. 3.

Referring to FIG. 3, a synthetic probe, designated "791," has a sequence complementary to a portion of the *S. arizona* (and *E. coli*) 23S 1405-1597 region, also shown in FIG. 3. Probe 791 has been shown in dot blot analysis, using the same Salmonella and non-Salmonella strains used above (and throughout this study), to exhibit inclusivity characteristics complementary to those exhibited by probe 414. That is, together the two probes hybridize (detect) the rRNAs of all Salmonella strains included in our test panels (i.e., are 100% inclusive for Salmonella, including a number of Salmonella belonging to a recently described new Salmonella group—group VI). The hybridization profile of probe 791 is not strictly complementary to that of probe 414; while hybridizing to Salmonella strains to which probe 414 does not (as expected), it also hybridized quite strongly to many of the same bacterial strains as probe 414. This might be taken as evidence for sequence heterogeneity in the underlying rRNA populations of these bacterial strains— something which has not been previously observed. The poor exclusivity characteristics of probe 791 preclude its use in most of the assay formats described above, with the exception of the dual specific capture/detection strategy which has been described above and is described in more detail below.

Variants of probe 791 can be designed to "match" the behavior characteristics of other probes of the probe sets in which probe 791 (or derivatives thereof) ultimately are utilized. Some of these are shown in FIG. 3.

Probes 414 and 791 have been tested to demonstrate the accessibility of their target regions, under a variety of solution hybridization assay formats as described above. Those tests have shown that the target regions are accessible to the probes in each case.

Figures 1, 4:
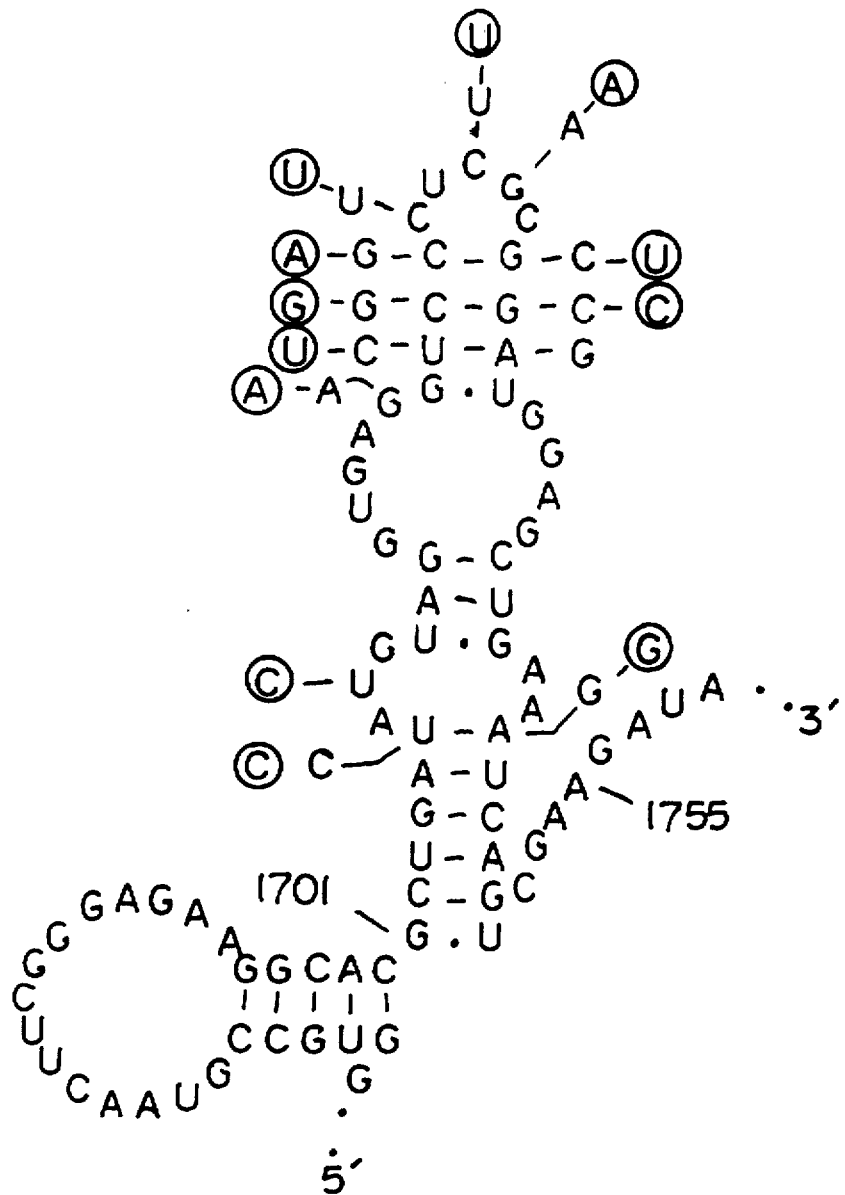

2) 23S rRNA region 1700-1760. This region is shown in FIG. 4, and consists of "Salmonella-specific" sequences concentrated between nucleotide 1712 and 1746.

Two predominant Salmonella-specific sequence patterns have been observed in this region. Pattern 1 is defined by the sequence derived from *S. typhimurium* strain e23566. Referring to FIG. 4, a probe designated "411", complementary to a portion of the pattern 1 sequence of this region has been constructed. Probe 411 has been subjected to dot blot (inclusivity and exclusivity) and solution hybridization (accessibility) testing, all of which indicate the usefulness of the probe, and derivatives, variants, and fragments thereof.

In dot blot tests, the 411 probe hybridized to the rRNAs of a significant number of Salmonella strains (317/323= 92%). Under these same conditions, the 411 probe does not hybridize to the rRNAs of a number of *S. arizona* strains tested (22 of the "misses" are to *S. arizona* strains) as predicted from the nucleotide sequence analysis discussed above. The remaining "misses" are to a mixture of "atypical" Salmonella belonging, mostly, to DNA homology group V.

The exclusivity characteristics of probe 411 were also tested by dot blot analysis. Hybridization to non-Salmonella bacteria was found to be restricted to a number of *C. freundii* and *C. diversus* strains, which variants of probe 411, were hybridized only weakly (FIG. 10).

Variants of probe 441 can be designed to "match" the behavior characteristics of other probes of the probe sets in which probe 441 (or derivatives thereof) ultimately are utilized. Some of these are shown in FIG. 3.

The second sequence pattern observed in the 1700-1760 region (pattern 2) is defined by the sequence derived from *S. arizona* strain RF908 (FIG. 4). It is sufficiently different from the pattern-1 sequence that RF908 is not detected by probe 411.

Referring to FIG. 4, synthetic probes, designated "690," "799," and "800," have sequences complementary to various portions of the *S. arizona* RF908 23S 1700-1760 region, also shown in FIG. 4. In a manner analogous to that of probe 791, described above, all complement the inclusivity profile of probe 411 to this target region. That is, probe 411 plus any one of probes 690, 799, or 800, together are 100% inclusive for all Salmonella in our reference collection. The three pattern 2-specific probes differ somewhat in their exclusivity behavior, with probe 800 exhibiting, by a slight margin, the best exclusivity profile at present. The combined exclusivity profiles of these various probe combinations can be seen in FIG. 9. Some cross hybridization to various *C. freundii* and *C. diversus* strains is evident. For some Salmonella diagnostic assays, this pattern of non-Salmonella cross hybridization may be acceptable either because, for example, these particular non-Salmonella bacteria are not standardly encountered in the particular application; or because the speed, sensitivity, cost efficiency, and/or inclusivity of the test rendered it economically feasible to retest the few positives that might be obtained.

Variants of these pattern-2 specific probes can be designed in order to "match" the behavior characteristics of other probes of the probe sets in which probe 411 (or derivatives thereof) ultimately are utilized. In particular, two of the probe sets described above are amenable to the dual specific oligo capture/detection assay format (also described above). Referring to FIG. 10, using probe 411 plus probe 800, for example, as oligo adenosine-tailed, target-capture probes, and probe 414 plus probe 791 as, for example, biotinylated detection probes, a probe "set" is created which, in this dual specific format, collectively detects all Salmonella (100% inclusivity) and virtually no non-Salmonella bacteria. (The reverse would also work, i.e., 414 plus 791 capture, and 411 plus 800 detection, but probably would result in less efficient capture due to the fairly extensive cross hybridization of probe 791).

Some low level of hybridization to certain *C. diversus* strains may be expected, but, because both the capture and detection probe sets each hybridize only weakly to *C. diversus*, the level of hybridization of the combined capture/detection probes to *C. diversus* will be acceptably small. A third Salmonella-specific sequence pattern, represented by *S. daressalaam*, also is shown in FIG. 4. Probe 802 is complementary to this third pattern.

Figures 1, 5:
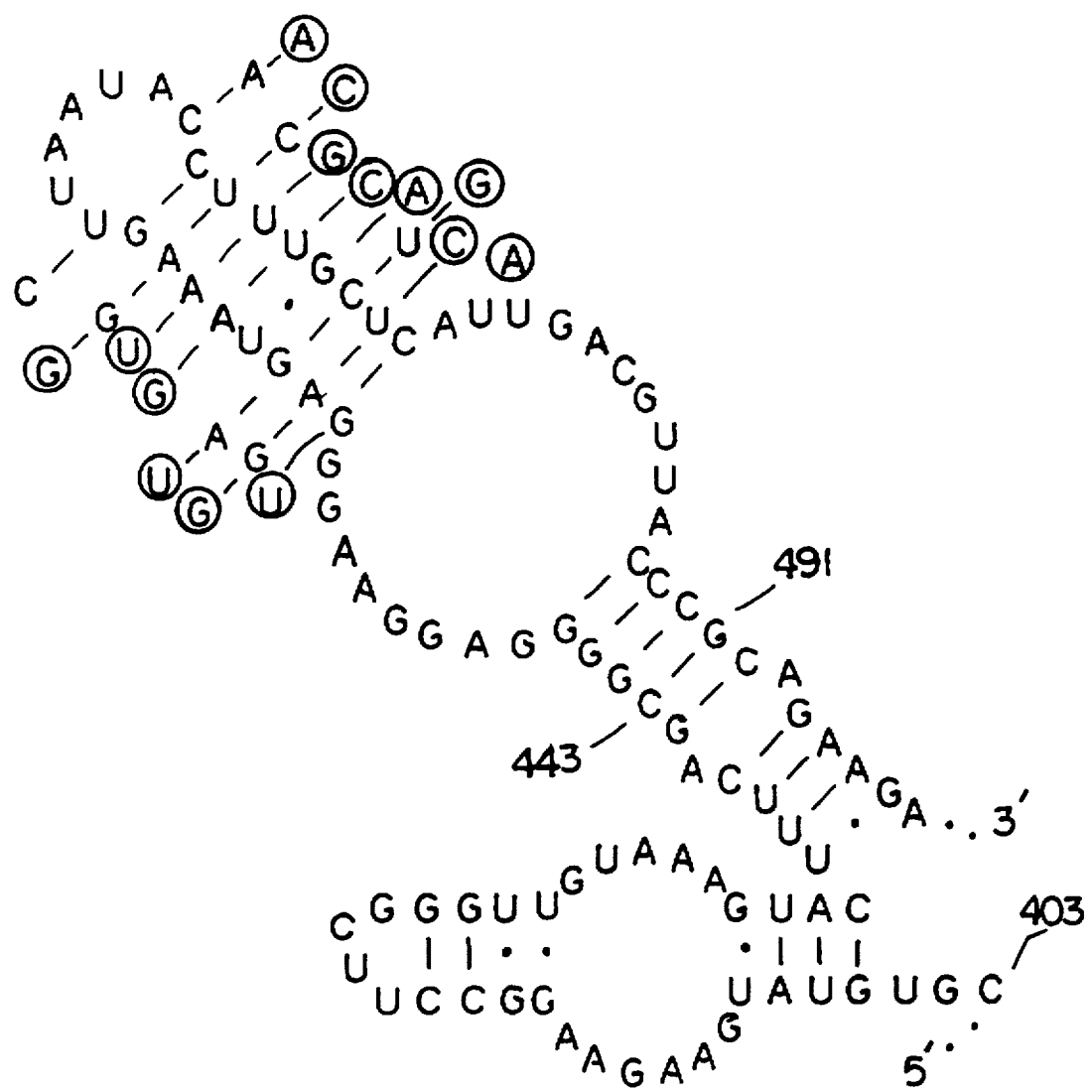

3) 16S rRNA region 430–510. This region is shown in FIG. 5, and consists of "Salmonella-specific" sequences concentrated between positions 455–477. Of the Salmonella strains whose 16S rRNA sequences have been obtained through this region, at least four different Salmonella-specific structural patterns have been observed (shown in FIG. 5). Pattern 1 was discovered initially from nucleotide sequence analysis of a cloned 16S rRNA gene from *S. typhimurium* e23566. Subsequent sequence analysis of this target region in the 16S rRNA from this and other Salmonella indicates that pattern 1 is widely represented within the genus.

Referring to FIG. 5, a number of synthetic probes, designated "643," "676," "778," "806," and "807," have sequences complementary to various portions of the pattern-1 containing 16S 430–510 region. All of these probes hybridize, with varying efficiencies, to the bulk of "typical" Salmonella (329/343 overall) but behave "spottily" against the "atypical" groups (groups IV, V, and VI) and fail to hybridize to 5/43 of our *S. arizona* isolates as well.

In terms of exclusivity behavior, these pattern-1 probes cross hybridize to some, but not all, strains of *Citrobacter freundii*, *C. diversus*, *Enterobacter cloacae*, and *E. sakazakii* (FIG. 10). Sequence analysis of this region from the 16S rRNA of these organisms indicates a closer evolutionary relationship between these species and the 'typical' Salmonella than is presently generally acknowledged.

The second Salmonella-specific sequence discovered in this target region (pattern 2) was derived from the 16S rRNA (and a 16S rRNA gene) of *S. arizona* (RF908). Pattern 2 is sufficiently different in nucleotide sequence from pattern 1 that, under hybridization conditions (stringencies) where probes to pattern 1 exhibit acceptable exclusivity behavior, they do not hybridize to pattern 2-containing rRNAs. So far, one probe specific to this target region pattern has been constructed (number 678, probe and target sequence given in FIG. 5) and tested. It hybridizes only to certain *S. arizona* strains. Probe 678 is extremely specific for its subset of *S. arizona* strains, hybridizing to no other Salmonella or non-Salmonella in our collection.

The third Salmonella-specific sequence discovered in this target region (pattern 3) was observed first in the 16S rRNA of *S. weslaco*. Subsequent sequence analysis of the 16S rRNAs of other Salmonella have revealed the presence of this pattern in a number of other strains including those of *S. bongor* and *S. riogrande*. Pattern 3 is very closely related to pattern 1 in primary sequence, differing from the latter at only one position (see FIG. 5). At the hybridization stringencies commonly employed (i.e., those experimentally determined to provide acceptable exclusivity behavior) this one nucleotide difference is enough to significantly diminish (ca. 6-fold), but not abolish, cross hybridization between pattern 1 probes (e.g., 676) and pattern 3 target sequences (e.g., *S. bongor*). At very high hybridization stringencies, or in formats employing a ribonuclense treatment step, this level of mismatching can easily be distinguished.

The fourth Salmonella-specific sequence pattern discovered in this target region (pattern 4) has been observed in one Salmonella species from our collection—a strain identified as CDC stk. N55 1925. By inference from the hybridization pattern of a probe specific for this pattern (probe 784, FIG. 5), it is a member of Salmonella group V. Probe 784 is quite specific for members of this group, exhibiting no significant hybridization to any other Salmonella or non-Salmonella bacteria in our collection. Thus, probe 784 like probe 678 described above, is highly exclusive and specific for a limited subgroup of Salmonella bacteria. Both probes can thus be used for subtyping Salmonella identified using other, broader specificity probes.

This 16S rRNA target region, and the one described immediately following (region 991–1045, FIG. 6) are the most highly variable which we have encountered in the Salmonella. Although this high level of sequence variability makes them potentially very useful for distinguishing various subgroups of Salmonella, the sequences characteristic of the bulk of the "typical" Salmonella are too similar to those found in a number of Citrobacter and Enterobacter species to usefully circumscribe the typical Salmonella. Thus, the determination that sequence variation exists in a particular region is not, in and of itself, sufficient to predict that an organism or group specific probe can be obtained.

Figures 1, 6:
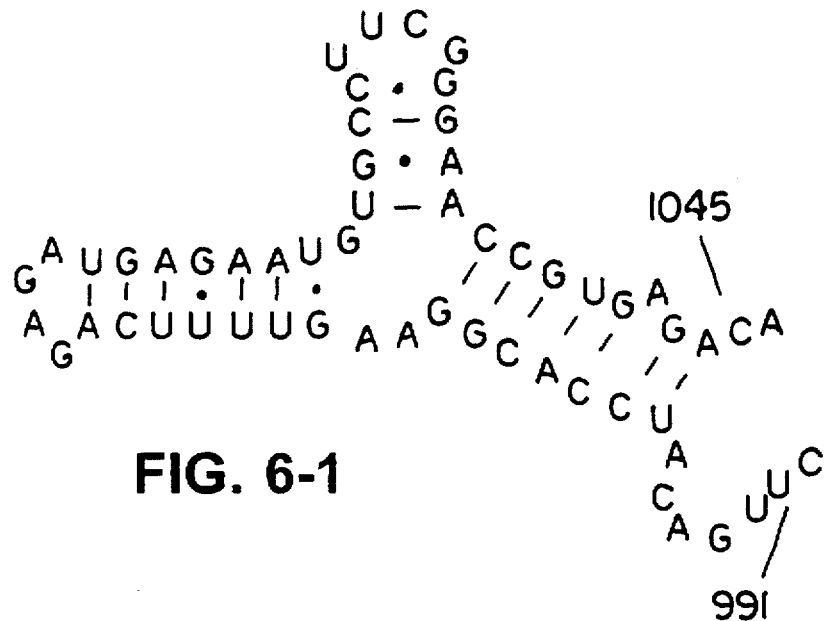

4) 16S region 991–1045. Referring to FIG. 6, two synthetic probes, designated "754," and "755," have sequences complimentary to the two main sequence patterns identified in 16S region 991–1045. Together, the two probes hybridize to most Salmonella in our collection but individually exhibit patterns of hybridization which reflect neither the established DNA homology groupings, nor the patterns exhibited by other sets of probes targeted at rRNA sequences. A number of Salmonella missed by both probes indicates that other, minor sequence patterns exist in this region among the Salmonella. Probes specific for these missed Salmonella could be designed.

Probe 754 individually hybridizes to many Salmonella, and only weakly to certain non-Salmonella strains, so that it (or derivatives thereof) could be used in conjunction with other probes as part of a Salmonella-specific probe set. Probe 755 exhibits strong and extensive cross hybridization to representatives of numerous and quite distinct non-Salmonella enteric bacteria. However, along with other of the non-exclusive "Salmonella" probes described herein, probe 755 could be useful as part of a broader specificity "Enteric-specific" probe set.

Figures 1, 7:
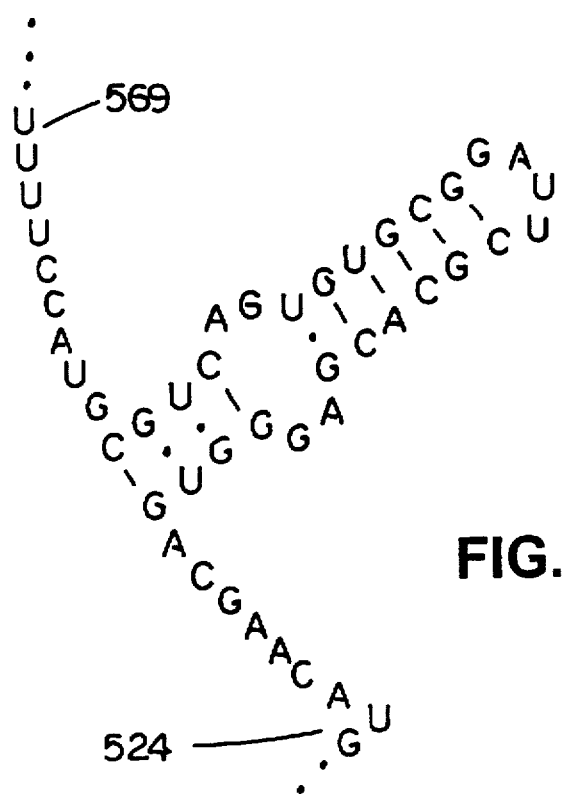

5) 23S rRNA region 512–560. This region is shown in FIG. 7, and consists of "Salmonella-specific" sequences concentrated between nucleotides 542–551. Analysis of this region has been especially difficult for two reasons. Some, but not all, Salmonella rRNA genes contain a large intron which interrupts the helical stem consisting of positions 532 to 560. This intron does not appear in the population of 23S rRNA molecules found in cells containing this gene structure. It would appear most likely that genes with this structure are inactive (data not shown). Second, direct reverse transcriptase sequencing of the 23S rRNA through this region indicates that, in at least some Salmonella, there are point sequence heterogeneities in a number of positions located within the 532–560 stem. Thus, cloning and sequencing multiple rRNA gene copies for certain Salmonella has been required to unambiguously determine nucleotide sequences through this region. In certain organisms, this region may be a recombinational "hot spot."

Referring to FIG. 7, two Salmonella-specific sequence patterns so far have been observed in this region. Pattern 1 is defined by the sequence derived from the rRNA of *S. typhimurium* strain e23566. Pattern 2 was derived from a non-intron-containing gene of *S. arizona* strain RF908. Both contain 2 "extra" nucleotides in the 532–560 stem, with respect to the E. coli sequence through this region and effectively lengthen the stem by one base pair. A set of probes, designated 848, 849 and 892, complementary to portions of the pattern 1 sequence of this region have been constructed. Probes 848 and 849 have been tested in the dot blot format for their ability to hybridize Salmonella and non-Salmonella bacteria. Both probes hybridizes to 68% (233/343) of Salmonella bacteria tested. Since many of these "misses" are to multiple strains of the same Salmonella species, this percentage is deceptively low. Additionally, 31 of the misses are to S. arizona strains, so pattern 1-complementary probes to this region perform reasonably well versus non-arizona, Salmonella species.

Still referring to FIG. 7, another set of probes, designated 893, 894, and 895, complementary to portions of the pattern 2 sequence of this region have been constructed and are undergoing testing.

Additional sequence patterns through this region likely exist in various Salmonella. Hybridization results using probes to patterns 1 and 2 will pinpoint Salmonella where these additional sequence patterns may be found. Variants of the above-described, 512–560 region probes can be designed to "include" these Salmonella. Also, variants of the 512–560 region probes can be designed to "match" the behavior characteristics of other probes of the probe sets in which these probes (or derivatives thereof) ultimately are utilized.

Other embodiments are within the following claims:

What is claimed is:

1. A method for detecting the presence of Salmonella bacteria in a sample, said method comprising the steps of:

contacting said sample with a probe of at least 25 nucleotides in length, said probe consisting of a nucleic acid sequence that is complementary or identical to any 25 or more consecutive nucleotides of the S. typhimurium 23S rRNA subunit between nucleotides 1474 and 1527 shown as pattern 2 in FIG. 3-2, the S. typhimurium 23S rRNA subunit between nucleotides 1707 and 1755 shown as pattern 1 in FIG. 4-2, the S. arizona 16S rRNA subunit between nucleotides 443 and 491 shown as pattern 2 in FIG. 5-2, the S. typhimurium 16S rRNA subunit between nucleotides 991 and 1045 shown in FIG. 6-2, or the 16S rRNA subunit of CDC stk. N55 1925 between nucleotides 443 and 491 shown as pattern 4 in FIG. 5-2 under conditions that permit said probe to hybridize to rRNA of Salmonella bacteria to form hybrid nucleic acid complex; and detecting said hybrid nucleic acid complex as an indication of the presence of Salmonella bacteria in said sample.

2. The method of claim 1 wherein said probe is complementary or identical to any 25 or more consecutive nucleotides of the S. typhimurium 23S rRNA subunit between nucleotides 1474 and 1527.

3. The method of claim 1, wherein said probe is complementary or identical to any 25 or more consecutive nucleotides of the S. typhimurium 23S rRNA subunit between nucleotides 1707 and 1755.

4. The method of claim 1, wherein said probe is complementary or identical to any 25 or more consecutive nucleotides of the S. arizona 16S rRNA subunit between nucleotides 443 and 491.

5. The method of claim 1, wherein said probe is complementary or identical to any 25 or more consecutive nucleotides of the S. typhimurium 16S rRNA subunit between nucleotides 991 and 1045.

6. The method of claim 1, wherein said probe is complementary or identical to any 25 or more consecutive nucleotides of the 16S rRNA subunit of CDC stk. N55 1925 between nucleotides 443 and 491.

7. The method of claim 1, wherein said probe is:
TCTGTGCATCCACTTCACTAAATGAGTAC-5';
TCCACACACAAGGTCCATTTAGGCCAAGTGAAATTGTGC-5';
CCCCCTCCTTCCACAACACCAATTATTGGCGTCGTTAACTGCAAT-5';
TCCTTCCACAACACCAATTATTGGCGTCGTTAACT-5';
TCCTTCCCCTATTCCGATTATTGGAACAAGTAACT-5';
ACTTCGCCAAATGGGCACCTCGACTTCAGTCAGCT-5';
GGTGTCTTCAAACGTCTCTACGCTTACACGGAAGC-5';
GGTGTCTTGAAAGGTCTCTACCTAACCACGGAAGC-5';
TCCACAACACCAATTATTGGCGTCGTTAAC-5';
CTCTTCCGCTGTTCCAATTATTGGAACAACTAACT-5';
CGACCAAAAGGTCCGTTTAGGCCTTTTAGTTCCG-5';
TGTACATCCACTTCGCCAAATGGGCAC-5';
TCGCCAAATGGGCACCTCGACTTCAGT-5';
CTGTGCATCCACTTCACCAAATGGGTA-5';
AAAGTCGCCCCTCCTTCCACAACACCAATT-5';
ATTGGCGTCGTTAACTGCAATGGGCGTCTT-5';
CGTGTCCAAATGGACACACTGACGCATG-5'; or
CACCCTCGTGTCCAAATGGACACACTGA-5'.

8. The method of claim 1, wherein said probe is TCTGTGCATCCACTTCACTAAATGAGTAC-5'.

9. The method of claim 1, wherein said probe is TCCACACACAAGGTCCATTTAGGCCAAGTGAAATTGTGC-5'.

10. The method of claim 1, wherein said probe is CGACCAAAAGGTCCGTTTAGGCCTTTTAGTTCCG-5'; or.

11. The method of claim 1, wherein said probe is TCGCCAAATGGGCACCTCGACTTCAGT-5'.

* * * * *